United States Patent [19]

Ippolito et al.

[11] Patent Number: 4,760,182
[45] Date of Patent: Jul. 26, 1988

[54] PROCESS FOR PREPARING SUBSTITUTED PHENOL ETHERS VIA OXAZOLIDINE-STRUCTURE INTERMEDIATES

[75] Inventors: Robert M. Ippolito, Thornhill; Stephen Vigmond, Toronto, both of Canada

[73] Assignee: Torcan Chemical Ltd., Aurora, Canada

[21] Appl. No.: 832,637

[22] Filed: Feb. 25, 1986

[51] Int. Cl.[4] ............... C07D 93/06; C07D 263/04
[52] U.S. Cl. .................................. 564/349; 548/215
[58] Field of Search ..................... 548/215; 564/349

[56] References Cited

U.S. PATENT DOCUMENTS

| Re. 27,822 | 11/1973 | Koppe et al. | 564/349 |
|---|---|---|---|
| 3,538,150 | 11/1970 | Gilman et al. | 564/349 |
| 3,541,130 | 11/1970 | Koppe et al. | 564/349 |
| 3,663,607 | 5/1972 | Barrett et al. | 548/215 |
| 4,018,778 | 4/1977 | Raabe et al. | 564/349 |
| 4,252,984 | 2/1981 | Manoury et al. | 564/349 |

FOREIGN PATENT DOCUMENTS 2130585  6/1984  United Kingdom .

OTHER PUBLICATIONS

Toran Chemical Ltd., CA 105-172044v.
Tonew et al., CA 89-190816d.

Primary Examiner—Donald G. Daus
Assistant Examiner—Cecilia Shen
Attorney, Agent, or Firm—Roylance, Abrams, Berdo & Goodman

[57] ABSTRACT

Phenol ethers such as 1-[4-[2-(cyclopropylmethoxy)ethyl]phenoxy]-3-[(1-methylethyl)amino]-2-propanol, otherwise known as betaxolol, of formula:

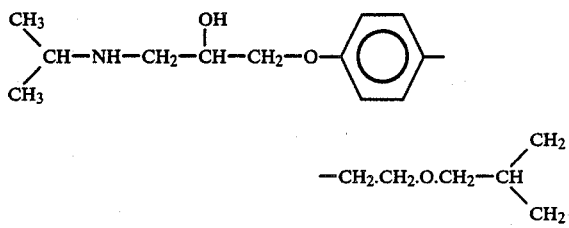

are prepared from p-hydroxyphenethyl alcohol by first reacting at the phenolic group, with epichlorohydrin followed by isopropylamine, to prepare the required secondary amine-hydroxy side chain. Protection of the alcoholic group is not required during these steps. Then the secondary amine-alcohol group is protected by reaction with a suitable aldehyde such as benzaldehyde to form an oxazolidine ring protectant whilst the alcohol chain is elaborated. The oxazolidine ring protectant is removed by simple acid hydrolysis.

6 Claims, No Drawings

PROCESS FOR PREPARING SUBSTITUTED PHENOL ETHERS VIA OXAZOLIDINE-STRUCTURE INTERMEDIATES

BACKGROUND OF THE INVENTION & PRIOR ART

This invention relates to organic chemical synthesis and more specifically to snythesis of pharmaceutical compounds.

The chemical compound 1-[4-[2-(cyclopropylmethoxy)ethyl]phenoxy]-3-[(1-methylethyl)amino]-2-propanol, hereinafter referred to as betaxolol, has recently been introduced and proposed for pharmaceutical use in human and veterinary therapy, in the cardiovascular field, mainly as a β-adrenergic blocking agent. It has the chemical formula:

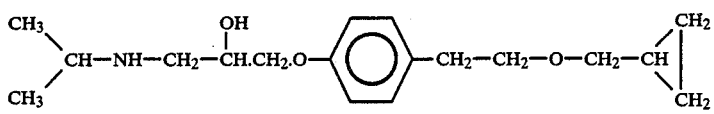

The family of compounds, including betaxolol, of the following general formula 1:

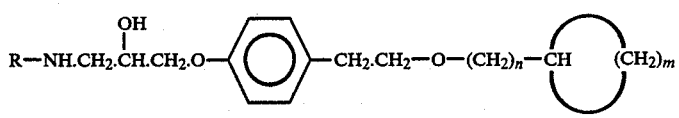

where m is an integer from 2 to 5, n is an integer from 1 to 4, and R is a branched alkyl of 3 or 4 carbon atoms, or cycloalkyl of 3 or 4 carbon atoms, racemic and optically active forms thereof, and pharmaceutically acceptable acid addition salts thereof, is described in Canadian Pat. No. 1,072,981 Synthelabo, together with methods for the preparation thereof.

The prior art synthesis of betaxolol starts with the readily available reagent p-hydroxyphenethyl alcohol, of formula:

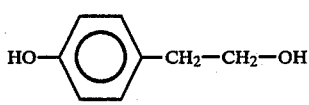

and converts this to the hydrochloride addition salt of betaxolol using a five step sequential synthesis. The more acidic phenolic hydroxyl is chemically blocked with a benzyl moiety e.g. by reaction of the phenoxide with benzyl chloride. In a second step, the hydroxyethyl group is then etherified by reaction with cyclopropylcarbinyl halide to give the desired species for the final product at this position. The phenolic position is then deprotected by hydrogenolysis and the phenolic position re-etherified with epihalohydrin to give a compound of formula:

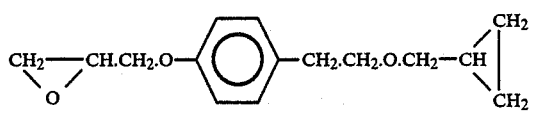

This fourth step product is then reacted with 2-aminopropane to yield betaxolol base. Thus, two of the five steps in the synthesis are the protection and de-protection of the phenolic hydroxyl. Each is a separate and necessary step.

It is an object of the present invention to provide a novel process for the preparation of betaxolol.

It is a further object to provide a process which avoids the costly and potentially hazardous hydrogenolysis of the prior art process described above and has the potential for a reduced number of synthetic steps.

It is a further object of the invention to provide novel chemical compounds useful as intermediates in the synthesis of betaxolol and similar compounds.

SUMMARY OF THE INVENTION

In the process of the present invention, p-hydroxyphenethyl alcohol is first elaborated at its phenolic terminus. The phenolic group thereof is so much more reactive than the primary alcohol group that the latter does not need protection while the phenolic terminus is elaborated. Firstly the p-hydroxyphenethyl alcohol is converted to its phenoxide anion with base, and then reacted with epihalohydrin, to produce a compound of formula I, thus:

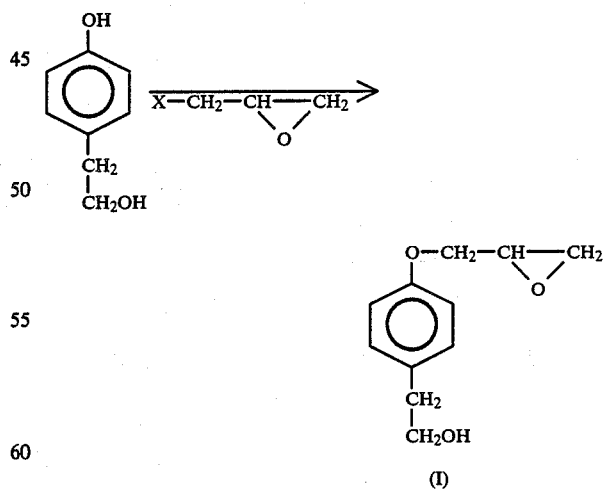

(I)

where X represents halogen, preferably chlorine, bromine or iodine. Next, the compound of formula I is reacted with a primary amine R.NH$_2$, where R is branched alkyl of 3–4 carbon atoms or cycloalkyl of 3–4 carbon atoms, to produce a compound of formula II, thus:

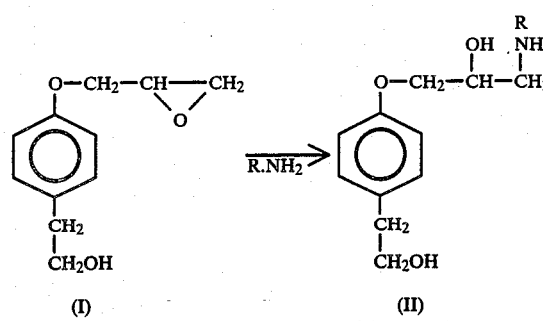

(I)  (II)

It is a significant advantageous feature of the process of the present invention that intermediate I does not need to be isolated or purified. One may just filter the inorganic by-products, remove solvent and excess alkylating agent and proceed to prepare intermediate II in the same reaction vessel.

Now to complete the elaboration of compound II into the desired phenol ether base, the secondary alcohol-amine grouping must be protected whilst the primary alcohol is appropriately etherified. In accordance with the present invention, this is accomplished by reaction of compound II with an appropriate aldehyde, to obtain a compound of general formula III below, thus:

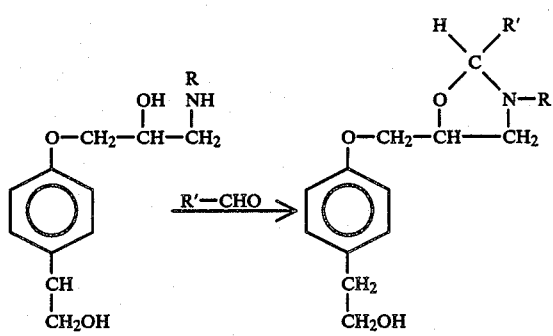

where R has the meaning given above and R' is aryl, substituted aryl, or $C_2$-$C_{11}$ straight chain or branched alkyl. It is not necessary to isolate compound II before its reaction to form intermediate III, so that once again the reaction may proceed in the same reaction vessel, after simple removal of solvents. The oxazolidine ring formed provides a stable but easily removable protecting group for the secondary alcohol-amine grouping required in the final molecule whilst the primary alcohol function is elaborated to form the desired final product.

The primary alcohol group is next etherified appropriately, e.g. with base and a cycloalkyl carbinyl halide, to produce protected phenol ether compound of formula IV, thus:

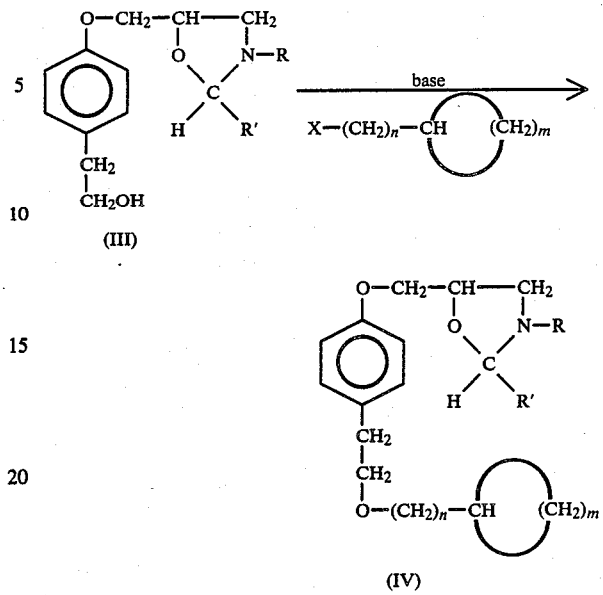

(III)

(IV)

Then in a final step, compound IV is subjected to acid hydrolysis, to effect deprotection and produce the final phenol ether base. This acid hydrolysis step can be performed as a separate step but is preferably conducted during the work-up of the preceding etherification step.

The process of the present invention thus avoids the unwanted hydrogenolysis step of the prior art process, with its attendant hazards and inconveniences. It provides a process scheme in which the overall number of synthetic steps is reduced to four (when deprotection is conducted during the work-up of the etherification of the primary alcohol). The steps can be conducted in rapid succession one after the other since there is no need to isolate and purify intermediate I, II, III or probably IV. It is merely necessary to filter the reaction mixture to remove solvents and reaction products dissolved therein, possibly to remove excess reagents by distillation from higher boiling solvents, and then proceed directly to the next stage of the process, at least in the cases of preparation of intermediates I, II, III and IV. In practical terms, therefore, the process is conducted in two steps, the first being the multi-stage preparation of intermediate IV from p-hydroxyphenethyl alcohol, and the second being the preparation and recovery of betaxolol or its analogues therefrom. Additionally, all steps provide high yield of desired product.

In the first step of the process, the p-hydroxyphenethyl alcohol is first converted to its phenoxide anion with base, in an appropriate solvent. The base can be chosen from among a wide variety, inorganic bases such as sodium carbonate, potassium carbonate, sodium hydroxide, potassium hydroxide, sodium hydride, potassium hydride etc. being most preferred. Examples of suitable solvents include acetonitrile, lower aliphatic alcohols (straight or branched chain), acetone, 2-butanone, tetrahydrofuran, dimethylformamide, dimethylsulphoxide benzene, toluene, etc. Reaction is suitably conducted under reflux. When the reaction is complete, the mixture is cooled, filtered, and excess solvent stripped off. Intermediate I forms as a white solid.

In the second step of the process, intermediate I is reacted with a primary amine $R.NH_2$. The choice of group R is dictated by the desired final product. In the preferred case of betaxolol preparation, R is isopropyl, and the amine reactant is isopropylamine. The process may be conducted without additional solvent, the reactant I being dissolved in the isopropylamine, and the reaction suitably being conducted under reflux. It is best to remove all residual amine from the mixture at the conclusion of this step of the process, e.g. by dissolving the compound in warm toluene, and removing it at reduced pressure, to minimize side reactions in subsequent steps of the process.

Intermediate II is protected by reaction with a suitable aldehyde, to form a compound having an oxazolidine ring, intermediate III. Oxazolidine formation is a reversible reaction requiring the removal of water to drive the reaction to completion. Thus, the preferred aldehydes are those of general formula R'—CHO, where R' is aryl, substituted aryl, or $C_2$-$C_{11}$ straight or branched alkyl group. Preferred are phenyl, lower alkyl substituted phenyl and $C_4$-$C_8$ straight chain alkyl groups. Most preferred, on account of its reaction efficiency and ready availability, is benzaldehyde, i.e. R' is phenyl. The reaction with banzaldehyde is clean, efficient, relatively fast, and yields an intermediate of satisfactory stability, but is in fact readily reversible under appropriate conditions. The reaction is conducted preferably in the presence of an inert solvent e.g. benzene or toluene, under reflux, and using a small molar (e.g. 10-25%) excess of benzaldehyde. Larger excesses of benzaldehyde tend to lead to faster completion of the reaction but lead to greater problems of subsequent removal of the excess benzaldehyde. Intermediate III thus formed need not be isolated and purified. The reaction mixture at the end of the reaction can be merely stripped under reduced pressure and pumped under vacuum to remove excess benzaldehyde.

In conversion of intermediate III to elaborate the primary alcohol chain, it is necessary to operate under basic conditions. Thus a base, such as lithium, potassium or sodium hydride or potassium t-butoxide etc. is added, followed by the appropriate compound of formula X—(CH$_2$)—CH (CH$_2$)$_m$ and a solvent. When the desired product is betaxolol, the reagent is cyclopropylcarbinyl halide (preferably the chloride). Preferred solvents are selected from dimethylsulfoxide, dimethylformamide, N-methyl-2-pyrrolidinone, glyme, tetrahydrofuran etc. Most preferred are polar aprotic solvents. The reaction proceeds satisfactorily at room temperature. The product, intermediate IV, may be isolated e.g. by pouring the reaction mixture into water, extracting with toluene, drying and evaporating but such isolation is not essential.

Finally, intermediate IV is subjected to acid hydrolysis to effect deprotection and form the final product e.g. betaxolol. This may be effected by treatment with an appropriate aqueous inorganic or organic acid with a cosolvent such as isopropanol. The product may be isolated and purified according to standard procedure.

The invention is further described and illustrated in the following non-limiting examples.

EXAMPLE 1

1-[4-(2-hydroxyethyl)phenoxyl]-2,3-epoxypropane 30.0 g p-hydroxyphenethyl alcohol, 60 g of anhydrous potassium carbonate and 50.28 g of epichlorohydrin were refluxed in 250 mL of acetonitrile for 5 hrs. After cooling, filtering and removing acetonitrile at reduced pressure, 300 mL of toluene were added and the toluene removed under reduced pressure. The residual oil solidifies on standing and is used directly in the next step. Yield=43.2 g, c. 100% yield. This solid after recrystallization in water has a melting point of 56°-58.5° C.

EXAMPLE 2

1-[4-[(2-hydroxyethyl)]phenoxy]-3[(1-methylethyl)amino]-2-propanol 10 g of 1-[4-(2-hydroxyethyl)phenoxy]-2,3-epoxypropane produced in Example 1 was refluxed in 50 mL of isopropylamine for 16 hrs. The amine was removed under reduced pressure, the residue dissolved in warm toluene and the toluene removed under reduced pressure. On standing the oil solidified. Yield=12.8 g (98%). After recrystallization in petroleum ether this solid had a melting point of 77°-78° C.

EXAMPLE 3

2-Phenyl-3-isopropyl-5-[4-[(2-hydroxyethyl)phenoxy]-methyl] oxazolidine 26.2 g of 1-[4-(2-hydroxyethyl)phenoxy]-3-[(1-methyl ethyl)amino]-2-propanol from Example 2, 12.96 g of benzaldehyde and 200 mLs of toluene were refluxed for 24 hours with azetropic removal of water. The solvent volume was reduced to 50 mLs during the final hour of reflux and the remaining solvent removed under reduced pressure. Yield=33.75 g (96% of yellow oil).

EXAMPLE 4

2-Phenyl-3-isopropyl-5-[[4-[2-(cyclopropylmethoxy)ethyl]phenoxy]methyl]oxazolidine 2.0 g of 2-Phenyl-3-isopropyl-5-[4-[(2-hydroxyethyl)phenoxy]methyl]oxazolidine from Example 3 was dissolved in 15 mLs of DMSO and added to 15 mLs of DMSO containing 0.78 g t BuO$^-$K$^+$. The solution was stirred for ½ hour and 0.64 g of chloromethylcyclopropane was added. After stirring 16 hrs. an additional 0.20 g of chloromethylcyclopropane and 0.33 g t-BuO$^-$K$^+$ were added and the stirring continued for 16 hrs, a final increment of 0.10 g of t-Buo$^-$K$^+$ was added and the stirring continued for 8 hrs. The reaction mixture was quenched into 150 mLs of water and the product extracted twice with 20 mLs of toluene. 2.25 g of yellow oil was obtained upon removal of the solvent under reduced pressure. Yield is 96% of the theoretical.

EXAMPLE 5

1-[4-[2-(cyclopropylmethoxy)ethyl]phenoxy]-3-[(1-methylethyl)amino]-2-propanol 2.25 g of 2-Phenyl-3-isopropyl-5-[[4-[2-(cyclopropyl methoxy)ethyl]phenoxy]methyl]oxazolidine from Example 4 was dissolved in a mixture of 10 mLs isopropanol, 10 mLs 5% aqueous hydrochloric acid. It was stirred at room temperature for 16 hrs. The isopropanol was removed under reduced pressure and 30 mLs 1% hydrochloric acid was added. The aqueous phase was washed with 15 mLs of toluene then basified and extracted twice with 10 mL portions of toluene. After removal of the solvent under reduced pressure 1.3 g of white solid was obtained (74% crude yield of betaxolol base). Betaxolol base was converted into its hydrochloride salt by dissolution in toluene and treatment with 1 equivalent of hydrochloric acid in isopropanol. Upon removal of isopropanol under reduced pressure and cooling of the toluene solution the hydrochloride salt of betaxolol was obtained. This solid is recrystallized twice from acetone, 4 mL/g, the second time with charcoal treatment to give a white crystalline solid with a melting point of 111.5°–112.5° C.

We claim:

1. A process for preparing phenol ethers of the formula:

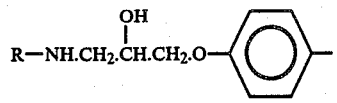

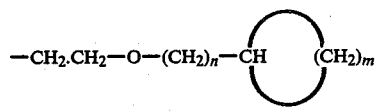

wherein m is an integer from 2 to 5, n is an integer from 1 to 4, and R is branched alkyl of 3 or 4 carbon atoms or cyclo-alkyl of 3 or 4 carbon atoms or a pharmaceutically acceptable salt thereof, from corresponding alpha-hydroxy-beta-(substituted phenol)ethanes, of formula II given below which consists essentially of:

(i) reacting a compound of formula II;

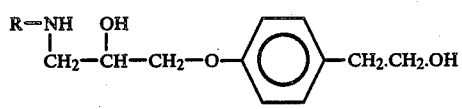

where R has the meaning given above with an aldehyde of formula R'—CHO where R' is phenyl, lower alkyl substituted phenyl or straight or branched $C_2$–$C_1$ alkyl to form an oxazolidine compound of formula III:

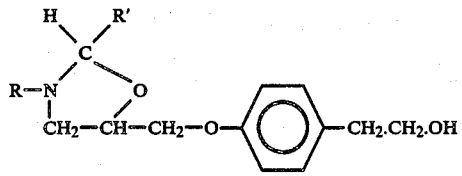

(ii) reacting the compound of formula (III) so prepared, without isolation or purification thereof, with a cycloalkylcarbinyl halide of general formula:

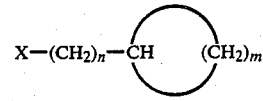

where X is a halogen, under basic conditions, to produce a compound of the general formula IV:

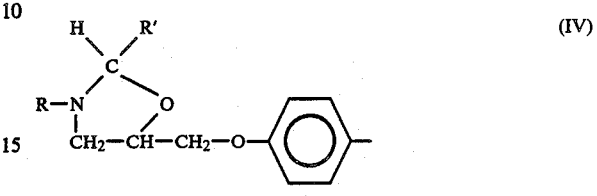

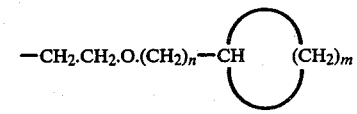

where R', R, N and m have the meaning given above, and (iii) subjecting said compound (IV) to acid hydrolysis to obtain said phenol ether and if necessary subsequently preparing the desired pharmaceutically acceptable salt therefrom.

2. The process of claim 1 wherein R represents 2-propyl, m is 2, and n is 1.

3. The process of claim 2 wherein R' is phenyl.

4. The process of claim 1 wherein the compound of formula II is prepared by reacting a compound of formula I

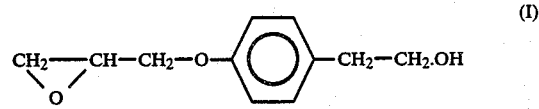

with a primary amine $R.NH_2$ where R is a branched alkyl of 3–4 carbon atoms or a cycloalkyl of 3–4 carbon atoms, but without isolation or purification of said compound of formula II.

5. The process of claim 4 wherein R is 2-propyl.

6. The process of claim 4 wherein the compound of formula I is prepared by reaction of p.hydroxyphenethyl alcohol with an epihalohydrin under basic conditions.

* * * * *